(12) United States Patent
Lee et al.

(10) Patent No.: US 6,432,641 B1
(45) Date of Patent: Aug. 13, 2002

(54) CONDUCTIVE METAL-CONTAINING NUCLEIC ACIDS

(75) Inventors: Jeremy S. Lee; Palok Aich, both of Saskatoon (CA)

(73) Assignee: University of Saskatchewan Technologies Inc., Saskatoon (CA)

( * ) Notice: Subject to any disclaimer, the term of this patent is extended or adjusted under 35 U.S.C. 154(b) by 0 days.

(21) Appl. No.: 09/213,052

(22) Filed: Dec. 16, 1998

(51) Int. Cl.[7] .......................... C12Q 1/68; G01N 15/00; C07H 21/00
(52) U.S. Cl. .......................... 435/6; 422/50; 422/68.1; 536/22.1; 536/25.3
(58) Field of Search .................. 422/50, 68.1; 435/6, 435/7.1; 536/22.1, 25.3

(56) References Cited

U.S. PATENT DOCUMENTS

| | | | |
|---|---|---|---|
| 4,562,157 A | 12/1985 | Lowe et al. | 435/291 |
| 5,278,043 A | 1/1994 | Bannwarth et al. | 536/23.1 |
| 5,556,752 A | 9/1996 | Lockhart et al. | 435/6 |
| 5,561,071 A | 10/1996 | Hollenberg et al. | 437/1 |
| 5,591,578 A | 1/1997 | Meade et al. | 435/6 |
| 5,679,647 A | 10/1997 | Carson et al. | 514/44 |
| 5,705,348 A | 1/1998 | Meade et al. | 435/6 |
| 5,770,369 A | 6/1998 | Meade et al. | 435/6 |
| 5,780,234 A | 7/1998 | Meade et al. | 435/6 |
| 5,780,448 A | 7/1998 | Davis | 514/44 |
| 5,804,566 A | 9/1998 | Carson et al. | 514/44 |
| 5,824,473 A | 10/1998 | Meade et al. | 435/6 |
| 5,830,877 A | 11/1998 | Carson et al. | 514/44 |

OTHER PUBLICATIONS

Roesler, W.J. et al, "The Liver–enriched Transcription Factor D–site–binding Protein Activates the Promoter of the Phosphoenolpyruvate Carboxykinase Gene in Hepatoma Cells" (1992), 267 (29) J. Biol. Chem., p. 21235–21243.

Lilley, D.M.J. & Clegg, R.M., "The Structure of the Four–Way Junction in DNA" (1993), 22 Annu. Rev. Biophys. Biomol. Struct., p. 299–328

Seeman, N.D. & Kallenbach, N.R., "DNA Branched Junctions" (1994), 23 Annu. Rev. Biophys. Biomol. Struct., p. 53–86.

Brunger, A.T. *X–PLOR Manual, Version 3.1: A System for X–ray Crystallography and NMR* (1993), Yale University Press.

Braun, R.P. & Lee, J.S., "Immunogenic Duplex Nucleic Acids are Nuclease Resistant" (1988), 141(6) J. Immunol., p. 2084–2089.

Swaminathan, V. & Sundaralingam, M., "The Crystal Structures of Metal Complexes of Nucleic Acids and Their Constituents" (1979), 14 CRC Crit. Rev. Biochem. Mol. Biol., p. 245–336.*

DeMeester, P. et al, "X–Ray Evidence for Adenine N(1)–Metal Bonding in a Cobalt–9–Methyladenine Complex" (1973), 324 Biochem. Biophys. Acta, p. 301–303.*

McCall, M.J. & Taylor, M.R., "Crystal Structure of a Zinc–(9–Methyladenine) Complex with N1 as the Preferred Binding Site" (1975), 390 Biochem. Biophys. Acta, p. 137–139.*

(List continued on next page.)

*Primary Examiner*—Ardin H. Marschel
(74) *Attorney, Agent, or Firm*—Townsend and Townsend and Crew, LLP

(57) ABSTRACT

The invention provides conductive polymers comprising metal-containing nucleic acid duplexes electrically coupled to an electron source. Methods for making conductive metal-containing nucleic acid duplexes are provided, comprising subjecting a nucleic acid duplex to basic conditions in the presence of a divalent metal cation. Methods of using conductive metal-containing nucleic acid duplexes are provided, including methods of genomic analysis, methods of molecular screening and immunological methods that produce antibodies to such molecules.

76 Claims, 7 Drawing Sheets

OTHER PUBLICATIONS

Lever, A.B.P., in: *Inorganic Electronic Spectroscopy* (1988), Elsevier; at p. 503–542.

Cheung, H.C., "Resonance Energy Transfer" in: *Topics in Fluoresence Spectroscopy vol. 2: Principles* (1991), Plenum (J.R. Lakowicz, ed.); at p. 127–176.

Clegg, R.M., "Fluorescence Resonance Energy Transfer and Nucleic Acids" (1992) 211 Methods in Enzymology, p. 353–371.

Murphy, C.J. et al, "Long–Range Photoinduced Electron Transfer Through a DNA Helix" (1993), 262 Science, p. 1025–1029.

Lewis, F.D. et al, "Distance–Dependent Electron Transfer in DNA Hairpins" (1997), 277 Science, p. 673–676.

Taubes, G., "Double Helix Does Chemistry At a Distance– But How?" (1997), 275 Science, p. 1420–1421.

Lee, J.S. et al, "A cooperative conformational change in duplex DNA induced by $Zn^{2+}$ and other divalent metal ions" (1993), 71 Biochem. Cell Biol., p. 162–168.

Paleček, E., "Local Supercoil–Stabilized DNA Structures" (1991), 26(2) CRC Crit. Rev. Biochem. Mol. Biol., p. 151–226.

Yagil, G., "Paranemic Structures of DNA and their Role in DNA Unwinding" (1991), 26 (516) CRC Crit. Rev. Biochem. Mol. Biol., p. 475–559.

Dandliker, P.J. et al, "Oxidative Thymine Dimer Repair in the DNA Helix" (1997), 275 Science, p. 1465–1468.

Hall, D.B. et al. "Oxidative DNA Damage Through Long– Range Electron Transfer" (1996), 382 Nature, p. 731–735.

Arkin, M.R. et al, "Rates of DNA–Mediated Electron Transfer Between Metallointercalators" (1996), 273 Science, p. 475–480.

\* cited by examiner

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 1
gtcacgatgg cccagtagtt                                                   20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 2
aactacttgg ccatcgtgac                                                   20

<210> SEQ ID NO 3
<211> LENGTH: 54
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 3
gctatgatcc aaaggccggc cccttacgtc agaggcgagc ctccaggtcc agct            54

<210> SEQ ID NO 4
<211> LENGTH: 54
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 4
agctggacct ggaggctcgc ctctgacgta aggggccggc ctttggatca tagc            54
```

CONDUCTIVE METAL-CONTAINING NUCLEIC ACIDS

FIELD OF THE INVENTION

The invention is in the field of conductive polymers, particularly conductive nucleic acids, such as DNA, as well as methods for producing and using such compounds.

BACKGROUND OF THE INVENTION

Polymeric molecular conductors are known. For example, some naturally occurring proteins facilitate electron transfer in such fundamental biological processes as photosynthesis and respiration. Electron transfer in such systems is generally understood to occur as the result of quantum mechanical 'tunnelling' of electrons along pathways, molecular orbitals, that connect one atom to the next in the polymer.

It has been proposed that the stacked aromatic bases of DNA may act as a 'π-way' for the transfer of electrons (Dandliker et al., 1997; Hall et al., 1996; Arkin et al., 1996). This proposal is based on a theory that the stacked arrangement of bases on complementary strands juxtaposes the shared electrons in the π orbitals of the aromatic nitrogen bases, facilitating quantum mechanical tunnelling along the stack of base pairs. A number of experiments have supported the view that this effect exists, while other experiments have provided contrary evidence that the effect is limited or non-existent.

For example, experiments have been reported to demonstrate that photoinduced electron transfer may occur between two metallointercalators tethered at either end of a 15-base pair DNA duplex (Murphy et al., 1993). On the other hand, kinetic analysis of distance-dependent electron transfer in a DNA hairpin has been used to show that DNA is a poor conductor, only somewhat more effective than proteins as a conductor of electrons (Lewis et al., 1997; Taubes, 1997).

U.S. Pat. Nos. 5,591,578; 5,705,348; 5,770,369; 5,780,234 and 5,824,473 issued to Meade et al. on, respectively, Jan. 7, 1997, Jan. 6, 1998, Jun. 23, 1998, Jul. 14, 1998 and Oct. 20, 1998 (and incorporated herein by reference) disclose nucleic acids that are covalently modified with electron transfer moieties along the nucleic acid backbone. Meade et al. teach that such modifications are necessary for nucleic acids to efficiently mediate electron transfer.

The theory of π-orbital-mediated conductance along a nucleic acid duplex suggests that, as a precondition, such conductance requires a stable duplex with stacked base pairs. The effect on duplex stability of the binding of metal ions to nucleic acids, particularly DNA, has been studied extensively for nearly 40 years. In general, cations that bind primarily to the phosphate backbone will stabilize the duplex conformation, whereas those that bind to the bases will tend to denature the duplex. These effects are readily demonstrated with thermal denaturation profiles (Tm measurements). Experiments of this sort show that most monovalent cations, such as $Na^+$, which tend to interact with the phosphate backbone, stabilize the duplex. This effect is reflected in the finding that there is approximately a 12° C. increase in Tm for each 10-fold increase in monovalent cation concentration (Marmur and Doty 1962). An exception to this general principle is $Ag^+$, which binds tightly to nitrogen bases, destabilizes the duplex, and therefore decreases the duplex Tm (Guay and Beauchamp 1979). Similarly, multivalent ions, particularly polyamines, which interact with the phosphate backbone are very effective duplex stabilizers.

For divalent metal cations, a series can be written in increasing order of DNA destabilization: $Mg^{2+}$, $Co^{2+}$, $Ni^{2+}$, $Mn^{2+}$, $Zn^{2+}$, $Cd^{2+}$, $Cu^{2+}$ (Eichorn 1962; Eichorn and Shin 1968). At one end of the spectrum, $Mg^{2+}$ increases the Tm at all concentrations; at the other end of the spectrum, sufficiently high concentrations of $Cu^{2+}$ will lead to complete denaturation of the duplex at room temperature (Eichorn and Shin 1968). This series also correlates with the ability of the divalent cations to bind to the bases (Hodgson 1977; Swaminathan and Sundaralinghamn 1979).

Cations are also involved in promoting several other structural transitions and dismutations in nucleic acids. It has previously been reported that $Zn^{2+}$ and some other divalent metal ions bind to duplex DNA at pHs above 8 and cause a conformational change (Lee et al., 1993). Preliminary characterization of the resulting structure incorporating zinc showed that it retained two antiparallel strands but that it was distinct from normal 'B' DNA: it did not bind ethidium bromide, it appeared to lose the imino protons of both A-T and G-C base pairs upon addition of a stoichiometric amount of $Zn^{2+}$, and it contained at least 5% fewer base pairs per turn than 'B' DNA.

SUMMARY OF THE INVENTION

The invention provides an electrical conductor comprising an electron source electrically coupled to a conductive metal-containing nucleic acid duplex (CM-CNA). An electron sink may also be electrically coupled to the CM-CNA. The CM-CNA comprises a first strand of nucleic acid and a second strand of nucleic acid. The first and the second nucleic acid strands include a plurality of nitrogen-containing aromatic bases covalently linked by a backbone (the backbone may be made up of phosphodiester bonds, as in DNA or RNA, or alternative structures as discussed below). The nitrogen-containing aromatic bases of the first nucleic acid strand are joined by hydrogen bonding to the nitrogen-containing aromatic bases of the second nucleic acid strand. The nitrogen-containing bases on the first and the second nucleic acid strands form hydrogen-bonded base pairs in stacked arrangement along the length of the CM-CNA. At least some, and preferably each, of the hydrogen-bonded base pairs comprises an interchelated divalent metal cation coordinated to a nitrogen atom in one of the aromatic nitrogen-containing bases.

The electron source electrically coupled to the CM-CNA may be an electron donor molecule capable of donating an electron to the conductive metal-containing nucleic acid duplex. Similarly, the electron sink may be an electron acceptor molecule capable of accepting an electron from the CM-CNA. The electron donor molecule may be a fluorescent molecule, such as fluorescein. Similarly, the electron acceptor molecule may be a fluorescent molecule, such as rhodamine. It will be appreciated that some molecules may act both as electron donors and electron acceptors in various embodiments of the invention.

The CM-CNA may be made of deoxyribonucleic acid strands, which together produce metal-containing DNA ("M-DNA"). The nitrogen-containing aromatic bases in the nucleic acid may be the naturally occurring bases: adenine, thymine, guanine and cytosine.

In various embodiments, the divalent metal cation used to make CM-CNA may be $Zn^{2+}$, $Co^{2+}$, or $Ni^{2+}$. Some divalent metal cations will not produce CM-CNA, and the present invention provides simple assays to determine whether a particular divalent metal cation will work to produce CM-CNA.

The divalent metal cations may be substituted for the imine protons of aromatic nitrogen-containing bases in the CM-CNA. In one embodiment, the divalent metal cations may be substituted for the N3 imine proton of thymine, or the imine protons of the N1 nitrogen atom of guanine.

The invention provides a method for making conductive metal-containing nucleic acid duplexes. A nucleic acid duplex is subjected to basic conditions in the presence of a divalent metal cation under conditions effective to form a conductive metal-containing nucleic acid duplex. Electron sources and sinks may be electrically coupled to the conductive metal-containing nucleic acid duplex, which may take the form of various embodiments discussed above.

The invention provides a method for detecting the formation of conductive metal-containing nucleic acid duplexes from first and second nucleic acid strands. The nucleic acid strands are mixed under conditions which allow complementary stands to hybridize and subjected to basic conditions in the presence of a divalent metal cation under conditions effective to form a conductive metal-containing nucleic acid duplex if the first and second strands are complementary. An electron source is provided electrically coupled to the conductive metal-containing nucleic acid duplex. Conductance of electrons between the electron source and the conductive metal-containing nucleic acid duplex is then tested to determine whether a CM-CNA has formed. The CM-CNA may take the form of various embodiments discussed above.

CM-CNAs of the invention may be used to carry electrons. They may also be used to raise antibodies in an animal, producing antibodies to CM-CNA. This latter use takes advantage of the finding that in some embodiments and under certain conditions CM-CNAs may be nuclease resistant.

DETAILED DESCRIPTION OF THE INVENTION

Figure 1:
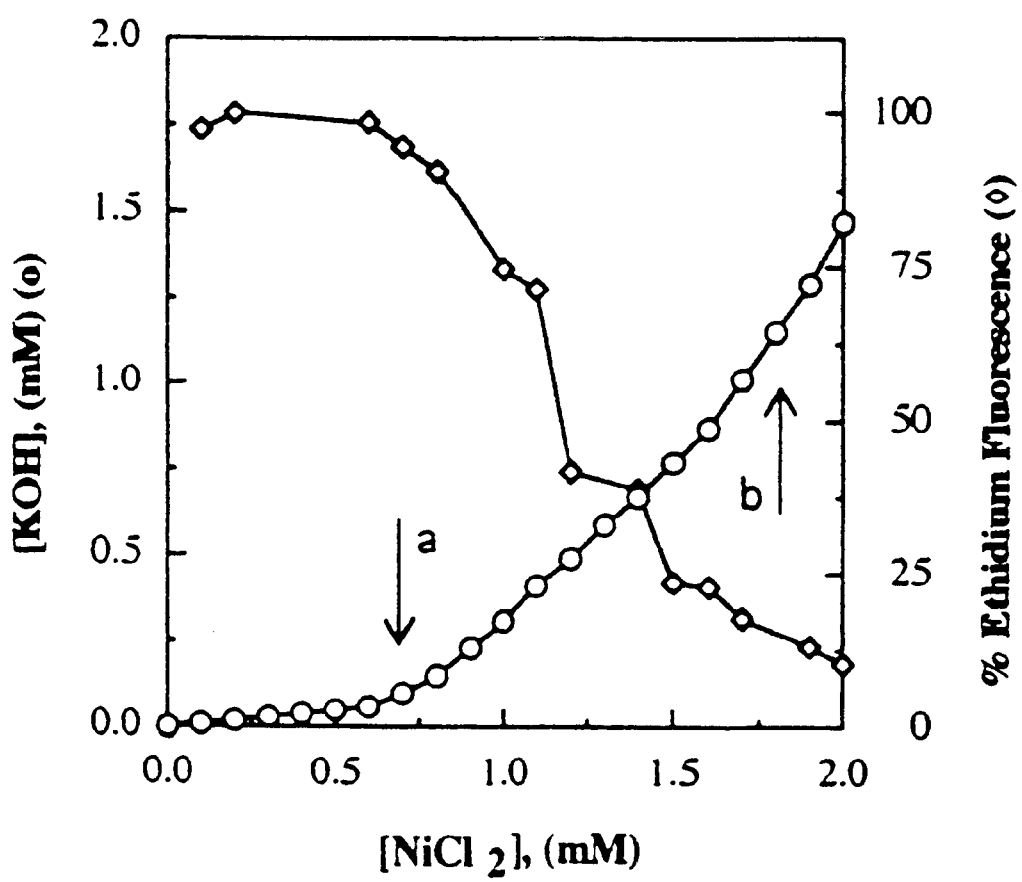
FIG. 1: shows the release of protons on formation of M-DNA. Upon addition of $NiCl_2$, protons are released and KOH was added (left axis) to maintain the pH at 8.5. After each addition 10 μl was removed to assess the formation of M-DNA by the ethidium fluorescence assay (Lee et al, 1993) (right axis). The experiment was performed in a 10 mL volume, with 1.1 mM in base pairs of calf thymus DNA. The DNA was dialyzed against water and sheared by passing through a 30 gauge needle five times. Arrow (a) indicates the putative point at which M-DNA formation began. This lag phase is proportional to the DNA concentration (data not shown) and may be due to the initial binding of the metal ion to the outside of the helix. Arrow (b) indicates the point at which 1.1 mM of $H^+$ had been released, beyond which precipitation of the M-DNA was observed.

The invention provides a CM-CNA duplex comprising an electron source electrically coupled to a nucleic acid duplex in which at least some of the stacked, aromatic nitrogen-containing base pairs chelate divalent metal cations. In such an embodiment, the metal-containing nucleic acid duplex acts as an electron acceptor, receiving electrons from the electron donor. In one embodiment of this aspect of the invention, the imine protons of a DNA duplex may be replaced by $Zn^{2+}$, $Co^{2+}$ or $Ni^{2+}$. The metal-containing DNA duplex may, for example be electronically coupled to molecular electron donors or electron sinks, such as fluorescein or rhodamine respectively, by covalent attachment.

In one aspect, the present invention provides a method for converting a nucleic acid duplex to CM-CNA. A nucleic acid duplex is treated with sufficient base in the presence of an adequate concentration of an appropriate divalent metal ion to result in the chelation of the divalent metal ion by the aromatic nitrogen bases of the nucleic acid. Such treatment is carried out for a sufficient period of time to produce a modified duplex comprising the divalent metal cation coordinated to nitrogen atoms in the aromatic nitrogen-containing bases of base pairs.

In one embodiment, conditions for converting DNA, such as a B-DNA, to M-DNA comprise subjecting the DNA to a solution at pH 8.5 or greater, with approximate concentrations of divalent metal ions as follows: 0.1 mM $Zn^{2+}$ or 0.2 mM $Co^{2+}$ or 0.2 mM $Ni^{2+}$. The conditions necessary to form M-DNA will vary depending on the metal ion or ions used and the nature of the nucleic acid. Those skilled in this art will appreciate that routine experiments may be carried out to determine appropriate conditions, varying parameters such as pH, nucleic acid concentration, metal ion concentration and the ratio of the metal ion concentration to the nucleic acid concentration. In some embodiments, a pH equal to or greater than 8, or greater than 8.5, may be required, and a suitable nucleic acid to metal ion ratio may be about 1:1.5 to about 1:2.0.

The CM-CNA may be electrically coupled to an electron source and an electron sink. For example, molecular electron donors and acceptors may act respectively as electron sources and electron sinks. In alternative embodiments, the electron donors and acceptors may be in solution, interacting transiently with the CM-CNA, or they may be in the form of a solid support, such as an electrode.

Solid phase supports to which the CM-CNA is attached may serve as electron sources, sinks or both. For example, immobilized arrays of CM-CNA may be prepared in accordance with the teaching of U.S. Pat, No. 5,556,752, issued Sep. 17, 1996 to Lockhart et al. (the "'752 Patent", incorporated herein by reference). Such immobilized arrays may then be used, as described therein and modified as necessary, to detect hybridization. In accordance with the present invention, the step of hybridizing the target nucleic acid to the immobilized probe may be followed, or accompanied, by the step of converting resulting duplexes to CM-CNA under basic conditions in the presence of a divalent metal cation, as described herein. Electron donors and acceptors may be provided in such a system, as described in the '752 Patent, so that the conductivity of the resulting CM-CNA duplex is detectable at the surface of the immobilization substrate, as is also described in the '752 Patent. It will be appreciated that such a system involves the use of CM-CNA as a conductor, which is one aspect of the present invention.

The formation of CM-CNA may be used to assay a variety of nucleic acid interactions. For example, the amplification of a target sequence using the polymerase chain reaction (PCR) may be assayed using methods of the present invention. In one aspect of such an assay, one PCR primer is provided with an electron donor moiety and the other PCR primer is provided with an electron acceptor moiety. In accordance with this aspect of the present invention, following PCR amplification cycles, the reaction mixture may be subjected to basic conditions in the presence of a divalent metal cation to promote the formation of CM-CNA. If the PCR amplification has been successful, CM-CNA will have formed and will be detectable as disclosed herein as a result of characteristic conductance between the electron donor and the electron acceptor. Unsuccessful amplification will leave the electron transfer moieties on the primers electrically uncoupled. In some embodiments, this approach may have the advantage of allowing detection of amplification without the need to separate the PCR primers from the PCR reaction mixture following amplification cycles. In accordance with this aspect of the invention, a kit may be provided comprising PCR primers having electron donors and electron acceptors, together with instructions for subjecting an amplification reaction mixture to basic conditions in the presence of a divalent metal cation to form CM-CNA. Such kits with appropriate instructions may also be provided for the other aspects of the invention disclosed herein Ligation of nucleic acids may also be assayed using methods of the present invention, wherein successful ligation is detectable by the formation of CM-CNA. In such a system, one of the nucleic acid duplexes to be ligated may be provided with an electron donor moiety, while the other nucleic acid duplex to be ligated is provided with an electron acceptor moiety. Ligation and subsequent formation of CM-CNA electrically couples the electron transfer moieties, producing a signal under appropriate conditions that is indicative of successful ligation. A kit may be provided for such a reaction, comprising an electron donor label and an electron acceptor label, together with instructions for coupling the electron donor and electron acceptor to nucleic acids that are to be ligated, and subjecting the ligation reaction mixture to basic conditions in the presence of a divalent metal cation to form CM-CNA.

In one embodiment of the invention, conditions are adapted to convert a B-DNA duplex to M-DNA. In one aspect of the invention, M-DNA is formed at pHs at or above 8 in the presence of sufficient amounts (preferably, in some embodiments, about 0.1 mM, provided the nucleic acid concentration is less than about 0.1 mM) of $Zn^{2+}$, $Ni^{2+}$ or $Co^{2+}$. In such an embodiment, $Mg^{2+}$ or $Ca^{2+}$ may not serve to produce M-DNA (Lee et al., 1993). A wide variety of bacterial and synthetic DNAs may dismutate to M-DNA under these conditions. In some embodiments, the process of M-DNA formation may be reversible by lowering the pH and/or addition of EDTA. In some embodiments, Ni-M-DNA requires EDTA to be converted to 'B' DNA at pHs greater than about 7. In some embodiments, poly[d(AT)] may not be convertible to M-DNA under such conditions. Unlike B-DNA, ethidium will not bind to some embodiments of M-DNA, and this property forms the basis of a rapid and sensitive "ethidium fluorescence assay" that may be used to monitor M-DNA formation (Lee et al., 1993).

M-DNA may be readily interconverted with B-DNA; therefore, useful techniques for manipulation of DNA such as cutting and splicing, and for the self-assembly of a variety of structures (such as two and three-way junctions) may be used with M-DNA forming sequences, as are well known in the art (Lilley and Clegg, 1993; Seeman and Kallenbach, 1994). In addition, the binding of sequence-specific proteins to CM-CNAs may be manipulated in some embodiments to interfere with conductance of the M-DNA so as to mimic electric switches and resistors.

Figure 6:
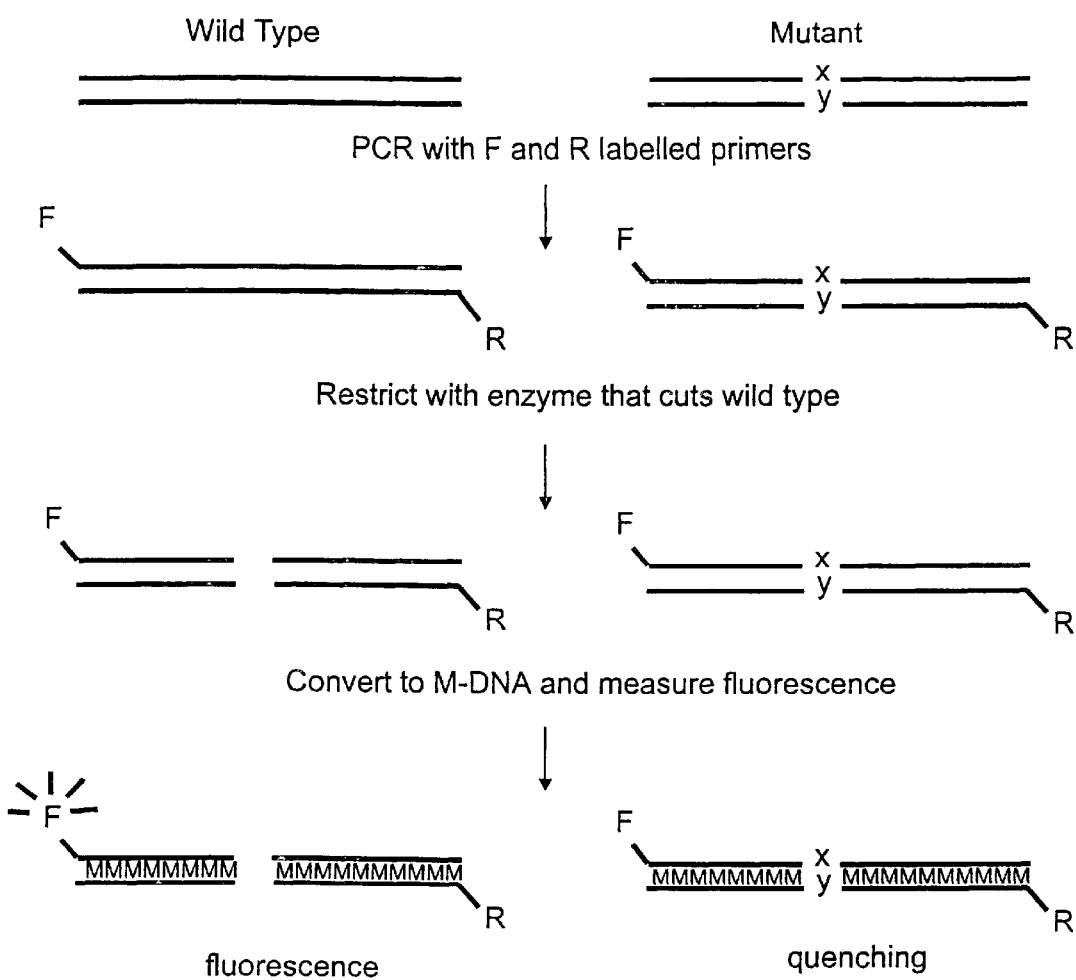
FIG. 6: is a schematic illustration showing as aspect of the invention that comprises a method of sequence analysis, in which one sequence that is susceptible to cutting by a restriction endonuclease may be distinguished from another sequence that is not susceptible on the basis of the presence or absence of conductance in an M-DNA duplex formed between an electron donor, shown as "F" for fluorescein in the figure, and electron acceptor, shown as "R" for rhodamine in the figure.

One aspect of the invention provides methods for detecting particular sequences in genomic analysis, such as methods for detecting particular mutations. In one such aspect of the invention, as shown in FIG. 6, the nucleic acid to be analysed (shown as wild type or mutant) is amplified by PCR using primers, one of the primers being labelled with an electron donor and the other being labeled with an electron acceptor, such as fluorescein (shown as "F") and rhodamine (shown as "R") respectively. Following amplification, the nucleic acid is treated with a restriction enzyme which may or may not cut the amplified sequence, depending upon the nature of the amplified sequence. For example, the restriction enzyme may only cut one allele of a gene, leaving other alleles or non-wild type sequences uncleaved (as shown in FIG. 6, where X and Y represent a mutant base pair). Following treatment with the restriction enzyme the amplified sequence may be subjected to conditions suitable for the formation of a CM-CNA, for example amplified DNA duplexes may be converted to M-DNA. The fluorescence of the sample may then be measured. If the amplified duplex spans the region between the primers, as in the mutant gene of FIG. 6, then the fluorescence of the amplified nucleic acid will be quenched by electron transfer along the CM-CNA. If, on the other hand, as in the wild type gene of FIG. 6, the amplified dupex has been cut by the restriction enzyme, the fluorescence of the electron donor will not be quenched. A sample in which half of the sequences formed CM-CNA and half did not, such as may be the case in an analysis of a sample from an individual with an autosomal recessive mutation, the degree of fluorescence may be intermediate. Sequence analysis in accordance with this aspect of the invention may be carried out in an automated fashion. For example, in one aspect this approach may simultaneously use multiple reaction wells to carry out such reactions, each well containing different reagents, such as different primers or different restriction enzymes, to yield an abundance of information about a particular sample in a relatively short time without the necessity of electrophoresis or other more time-consuming steps.

Figure 7:
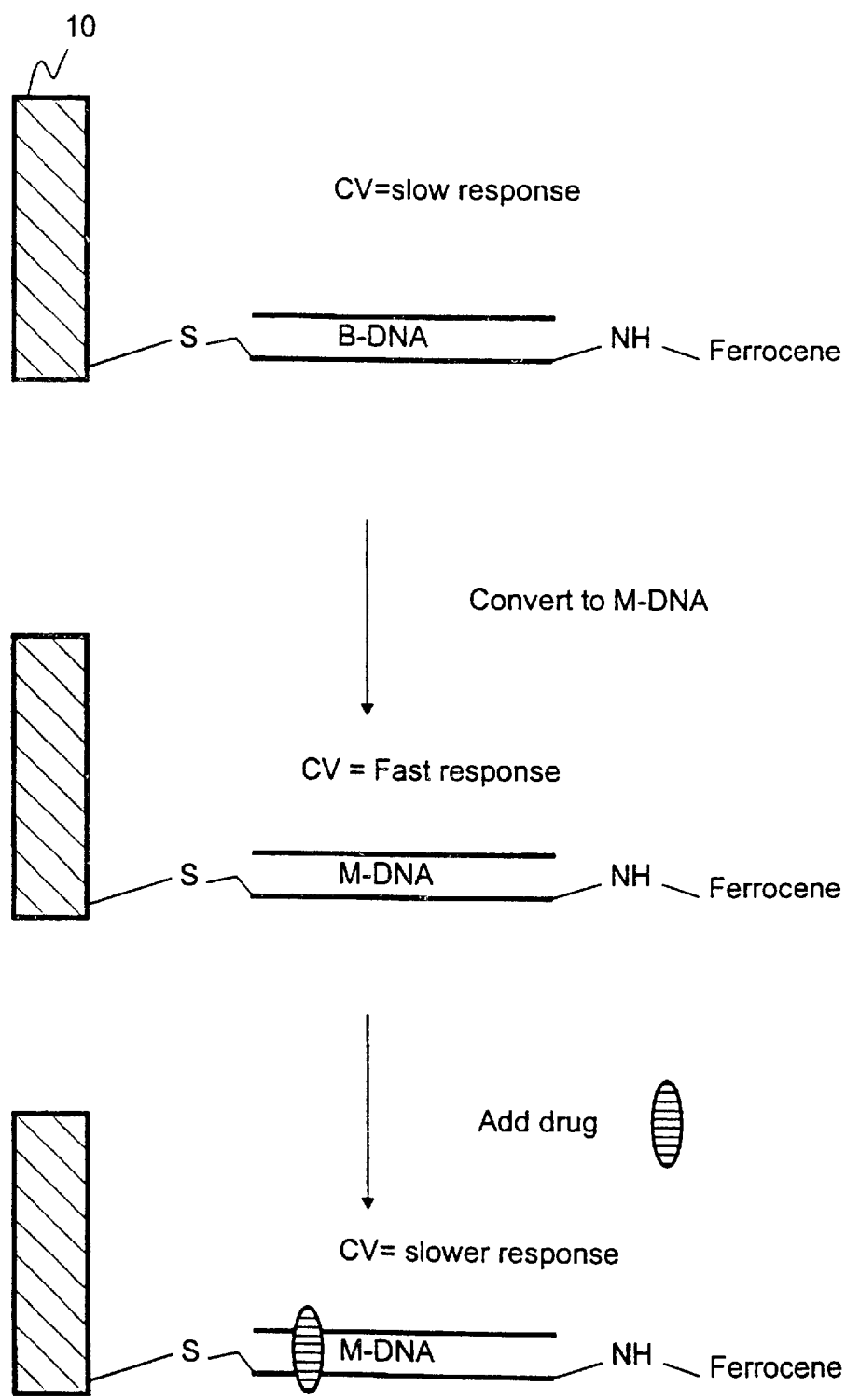
FIG. 7: is a schematic illustration showing a nucleic acid coupled to electrode 10 and subjected to conditions suitable to form M-DNA, while measurements are taken of the conductance of the CM-CNA by cyclic voltammetry, both in the absence and presence of a DNA-binding drug.

In an alternative aspect, the invention provides a sensor for monitoring the presence of nucleic acid binding moieties in a sample. In one embodiment of this aspect of the invention, as shown in FIG. 7, a nucleic acid duplex capable of forming a CM-CNA is attached between an electron sink and an electron donor, such as ferrocene, the nucleic acid is exposed to a sample under conditions that favour the formation of a CM-CNA duplex, the binding of a moiety to the nucleic acid is detected by a change in the conductance of the nucleic acid. For example, DNA binding molecules may convert M-DNA back to B-DNA under such conditions, and thereby prevent or reduce the CM-CNA mediated quenching of a fluorescent electron donor that is coupled to the nucleic acid. In one embodiment, the nucleic acid may be coupled to an electrode (for example as described in Braun et al., Nature, 391: 775–778, 1998, incorporated herein by reference), such as gold electrode 10 of FIG. 7, and the electrode may then be used to measure the conductance of the CM-CNA while the electrode is exposed to a sample. In some embodiments, for example, such conductance measurements may utilize cyclic voltammetry (shown as CV in FIG. 7). Such, assays involving the detection of variations in the conductance of a CM-CNA may be used in various embodiments of the invention to detect interactions between nucleic acids and a wide variety of other moieties, such as small molecules, triplex-forming oligonucleotides and DNA-binding proteins.

In some embodiments, the conductance of CM-CNAs may be enhanced by modification of the nucleic acid with electron transfer moieties, such as is taught in the following U.S. Pat. Nos. 5,591,578; 5,705,348; 5,770,369; 5,780,234 and 5,824,473 issued to Meade et al. on respectively Jan. 7, 1997, Jan. 6, 1998, Jun. 23, 1998, July 14, 1998 and Oct. 20, 1998 (and incorporated herein by reference).

In the context of the present invention, 'conductive' means capable of conducting electrons. An electron source in accordance with the present invention may be any compound or substance capable of providing electrons, such as an atomic or molecular conductor. Similarly, an electron sink (or acceptor) may be any compound or composition capable of accepting electrons. A nucleic acid duplex comprises hybridized strands of nucleic acid molecules. A strand of nucleic acid comprises at least two nucleotides covalently linked by a backbone. The backbone may be made up of polymeric phosphodiester bonds, as in DNA or RNA. Alternatively, other backbone structures may be effective to appropriately align the aromatic nitrogen-containing bases in a stacked arrangement capable of chelating metal ions and conducting electrons. For example, phosphoramide, phosphorothioate, phosphorodithioate, O-methylphosphoroamidite or peptide nucleic acid linkages may be effective to form such a backbone. Similarly, other components of the backbone may vary in accordance with the invention, encompassing deoxyribose moieties, ribose moieties, or combinations thereof. If RNA is used, those skilled in this art will appreciate that conditions must be adapted to account for the fact that RNA is labile in basic solution, so that conversion of RNA to CM-CNA may require modified reaction conditions which avoid hydrolysis of the RNA. In one aspect of the invention, the nitrogen-containing aromatic bases are preferably those that occur in native DNA and RNA: adenine, thymine, cytosine guanine or uracil. However, those skilled in this art will understand that alternative nitrogen-containing aromatic bases may be utilized, preferably they are capable of interchelating a divalent metal ion, coordinated to a nitrogen atom in the aromatic nitrogen-containing base and stacking, to produce a conductive metal-containing nucleic acid duplex. In accordance with these variations in the structure of the molecules of the invention, alternative divalent metal ions may be utilized, again depending upon the ability of such ions to participate with the other substituents of the molecules of the invention in the formation of a conductive metal-containing nucleic acid duplex. The present application sets out assays for the creation of such a duplex, so that others may routinely identify functional substitutions and variations in the structure of the molecules of the invention. Accordingly, although various embodiments of the invention are exemplified herein, other adaptations and modifications may be made within the scope of the invention. The following examples are merely illustrative of alternative embodiments of the invention and are not comprehensive nor limiting in their scope.

EXAMPLE 1

Conductance of CM-CNA

Figure 3:
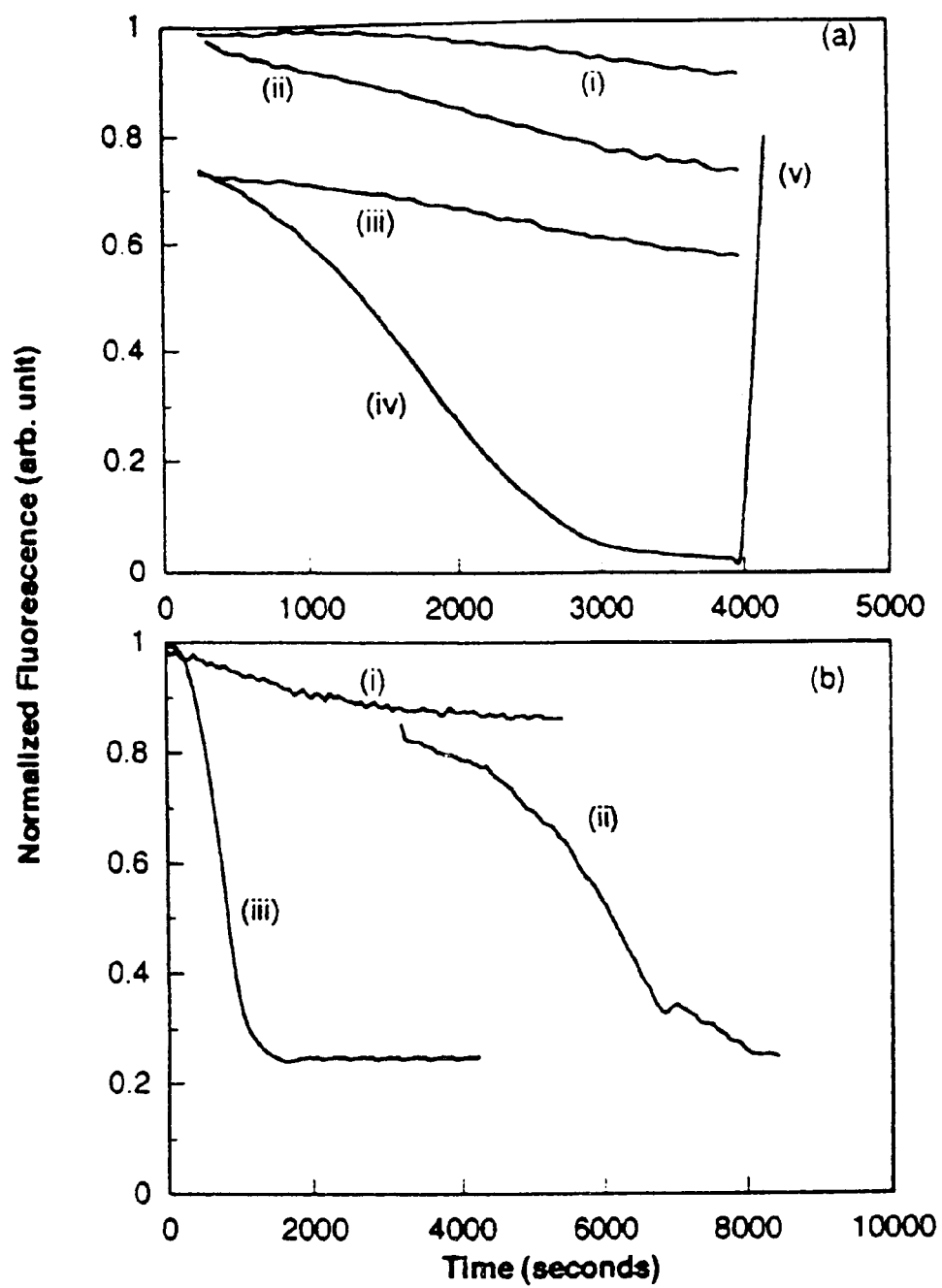
FIG. 3: shows the fluorescence of fluorescein-labelled oligonucleotides during the formation of M-DNA (see Table 1 for the sequences of the 20-mer and 54-mer) (a) Effect of $Zn^{2+}$ on the 20-mer duplex. (i) Fl-20-mer duplex without $Zn^{2+}$; (ii) Fl-20 mer duplex with $Zn^{2+}$; (iii) Fl-20-mer-Rh duplex in the absence of $Zn^{2+}$; (iv) Fl-20 mer-Rh duplex in the presence of $Zn^{2+}$; (v) addition of EDTA after the formation of M-DNA. (b) Effect of $Zn^{2+}$ on the 54-mer duplex. (i) Fl-54-mer-Rh with D-site binding protein (1 ug/ml) (the site is located at the centre of the 54-mer duplex) in the presence of $Zn^{2+}$; (ii) addition of proteinase K (50 ug/ml) after 3,000 seconds; (iii) Fl-54 mer-Rh duplex wit $Zn^{2+}$. The experiments were performed in 20 mM $NaBO_3$ buffer, pH 9.0 at 20° C. with 10 mM NaCl and 1 mM $Zn^{2+}$ as appropriate. Fluorescence intensities are normalized with respect to the fluorescence intensity of the Fl-20-mer-duplex either in the absence or presence of $Zn^{2+}$.

The conductance of CM-CNA was investigated by preparing duplexes of 20 base pairs of DNA with fluorescein (the electron donor) and rhodamine (the electron acceptor) at opposite ends of the duplex. Methods for such attachment are disclosed in Kessler, 1995, and Haugland, referenced below. Fluorescein and rhodamine fluoresce at different wavelengths, so that it is possible to distinguish fluorescence of the electron donor from fluorescence of the electron acceptor. Under conditions which favour B-DNA (pH less than about 8.0 in the presence of EDTA) the fluorescence of the fluorescein electron donor is partially quenched and the fluorescence of the rhodamine electron acceptor is partially enhanced. This appears to be an example of through space energy transfer (Forster resonance energy transfer or FRET) which has been well-documented in a number of different laboratories (Cheung, H. C. 1991 and Clegg, R. M., 1992). FRET quenching is understood to be due to dipole-dipole interactions along a molecule (not electron conductance) and is highly distance dependent (the effect decreasing with interatom distance in sixth order relationship: $1/r^6$); the value of 25% quenching measured for the 20 base pair duplex is in accordance with the expected FRET behaviour for this length of helix (Clegg, 1992). As shown in FIG. 3a, the fluorescence intensity is relatively stable at pH 9 although at long times there is some loss due to photobleaching.

On addition of $Zn^{2+}$ (1 mM) to the DNA (pH 9), the fluorescence is quenched up to 95% over a period of 1 hr. This rate of increasing quenching mirrors the known rate of formation of M-DNA under these conditions (Lee et al., 1993). Upon reformation of B-DNA by addition of an excess of EDTA (2 mM) after 4,000 sec., the quenching is rapidly reversed. These results are summarized in Table 1.

As a control, the 20-mer duplex (without metal ions) with a fluorescein label shows only a small decrease in intensity due to photobleaching, similar to the effect noted above with respect to ordinary B-DNA (FIG. 3a). Similarly a mixture of two duplexes, one labelled with fluorescein and the other labelled with rhodamine, show minimal quenching either as B-DNA or M-DNA (see Table 1).

To measure the fluorescence life time of the fluorescein when it is attached to the 20-mer oligonucleotide having fluorescein at one end and rhodamine at the other end, the fluorescein is irradiated with a picosecond pulse of laser light and the fluorescence decay of the excited fluorescein is then followed for several nanoseconds. Normally (as is the case with B-DNA) the t½ for decay is about 3 nanoseconds. Upon conversion to the $Zn^{2+}$ form of M-DNA as described above, the t½ drops to about 0.3 nanoseconds. This extremely fast decay is consistent with electron conductivity by the M-DNA helix.

Electron transfer in the $Zn^{2+}$ isomer of M-DNA was investigated in a longer helix of 54 base pairs (this 54 mer has an estimated length of over 150 Å). This 54 mer also contained the recognition site for the D-site binding protein (Roesler et al., 1992) in the middle of the sequence. As shown in FIG. 3b, there is no quenching in the absence of metal ions in the 54 mer, this may be because the fluorophores are well separated so that there is no FRET. However, upon addition of $Zn^{2+}$ under appropriate conditions to form M-DNA (1 mM $Zn^{2+}$, pH 9), the fluorescent intensity rapidly drops to 25% of the initial value, demonstrating efficient conductance over the length of the 54 mer.

In the presence of the D-site binding protein, under conditions appropriate to form M-DNA, the fluorescence intensity of the 54 mer only drops slowly. However, as judged from the ethidium fluorescence assay (Lee et al., 1993), the majority of the 54 mer DNA is in the form of M-DNA (which does not bind ethidium). This demonstrates that the D-site DNA-binding protein is interrupting the flow of electrons along the 54 mer M-DNA duplex. As a control, the D-site binding protein has no effect on the quenching of the 20-mer (which as no D-site binding sequence, see Table 1). On addition of protease at 3000 seconds to the D-site binding protein:54 mer M-DNA complex, the protein is cleaved and the fluorescence intensity begins to drop, eventually reaching the minimum value of 25% of the initial fluorescence value. This experiment is a simple example of a bioreactive electronic switch comprising CM-CNA and a DNA-binding protein capable of disrupting the conductive duplex. Such a switch is also analogous to an electronic memory element, having two interchangeable states, conductive and non-conductive.

TABLE 1

Normalized Fluorescence of the Fluorescein-labelled oligonucleotides

| Oligonucleotide | Treatment | Fluorescence |
| --- | --- | --- |
| Fl-20-mer duplex | none | 1 |
| Fl-20-mer duplex | $+Zn^{2+}$ | 0.98 |
| Fl-20-mer duplex | $+Zn^{2+}$ at pH 8.0 | 0.92 |
| Fl-20-mer single strand | none | 0.87 |
| Fl-20-mer duplex + Rh-20-mer duplex | none | 0.97 |
| Fl-20-mer-Rh duplex | none | 0.73 |
| Fl-20-mer-Rh duplex | $+Zn^{2+}$ | 0.05 |
| Fl-20-mer-Rh duplex | $+Zn^{2+}$ + EDTA | 0.87 |
| Fl-20-mer-Rh duplex | $+Zn^{2+}$ at pH 8.0 | 0.92 |
| Fl 20-mer-Rh duplex | $+Co^{2+}$ | 0.05 |
| Fl 20-mer-Rh duplex | $+Co^{2+}$ + EDTA | 0.7 |
| Fl 20-mer-Rh duplex | $+Ni^{2+}$ | 0.06 |
| Fl 20-mer-Rh duplex | $+Ni^{2+}$ + EDTA | 0.7 |
| Fl 20-mer-Rh duplex | $+Mg^{2+}$ | 0.83 |
| Fl 20-mer-Rh duplex | +D-site binding protein + $Zn^{2+}$ | 0.06 |
| Fl 54-mer-Rh | +D-site binding protein + $Zn^{2+}$ | 1 |
| Fl 54-mer-Rh | $+Zn^{2+}$ | 0.21 |

Conversion to M-DNA was performed in 20 mM $NaBO_3$ buffer, pH 9.0. Fluorescence assays were carried out in 20 mM Tris pH 8.0. Other conditions were as follows: 10 mM NaCl at 20 EC and 1 mM $Zn^{2+}$ or 0.2 mM $Co^{2+}$ or 0.2 mM $Ni^{2+}$ or 2 mM EDTA as appropriate. Excitation was at 490 nm with emission measured at 520 nm. Fluorescence intensities are normalized with respect to the fluorescence intensity of the Fl-20-mer-duplex either in the absence or presence of $Zn^{2+}$ and were measured after 3,000 sec.

Sequences and nomenclature: The oligonucleotides were labelled 5' with fluorescein (Fl) or rhodamine (Rh) using standard attachment methods and constructs, for example as used in DNA sequencing. The fluorescein 20-mer was as follows: SEQ ID 1: Fl-5'-d(GTC ACG ATG GCC CAG TAG TT). The rhodamine 20-mer was as follows: SEQ ID 2: Rh-5'-d(AAC TAC TGG GCC ATC GTG AC). The same unlabelled sequence was used to produce the Fl-20-mer-duplex. The Fl-54-mer was as follows: SEQ ID 3: Fl-5'-d (GCT ATG ATC CAA AGG CCG GCC CC T TAC GTC AGA GGC GAG CCT CCA GGT CCA GCT) (The D-site is underlined). The Rh-54 mer was as follows: SEQ ID 4: Rh-5'-d(AGC TGG ACC TGG AGG CTC GCC TCT GAC GTA AGG GGC CGG CCT TTG GAT CAT AGC). The same unlabelled sequence was used to produce the Fl-54-mer duplex.

This Example demonstrates a method for converting a nucleic acid duplex to a conductive metal-containing nucleic acid duplex, in this case M-DNA. The excited electron on the fluorescein is rapidly transmitted down the M-DNA helix to the rhodarnine; demonstrating rapid and efficient electron transfer along the M-DNA. The $Co^{2+}$ and $Ni^{2+}$ isomers of M-DNA show quenching of the fluorescein by up to 95% even in the absence of the rhodamine acceptor (Table 1). This indicates that the M-DNA can itself act as an electron acceptor.

EXAMPLE 2

Physical Properties of M-DNA

The mobility of linear or covalently closed circular forms of M-DNA in agarose gels is only slightly less than that of B-DNA (indicating that treatment in accordance with the invention to produce M-DNA need not cause condensation or aggregation of the DNA). NMR studies show that the imino protons of T (pKa 9.9) and G (pKa 9.4) may not be present in M-DNA, illustrating that the imine protons may be replaced by the divalent metal cation in M-DNA. The release of protons during the formation of M-DNA may be indicative of this phenomenon. As shown in FIG. 1, M-DNA begins to form at about 0.7 mM $NiCl_2$ (as judged from the ethidium fluorescence assay); there is a concomitant release of protons so that KOH may be added to maintain the pH at 8.5. At 1.8 mM $NiCl_2$, M-DNA formation is virtually complete and the complex starts to precipitate. This suggests that one proton is released per $Ni^{2+}$ atom per base pair during the formation of M-DNA. The $Zn^{2+}$ and $Co^{2+}$ isomers of M-DNA also release protons during formation, and precipitation of the complex may occur at a lower concentration of divalent metal ion than with $Ni^{2+}$. These results are consistent with the metal ion being coordinated to the N3 position of T and N1 of G in the base pairs.

Figure 2:
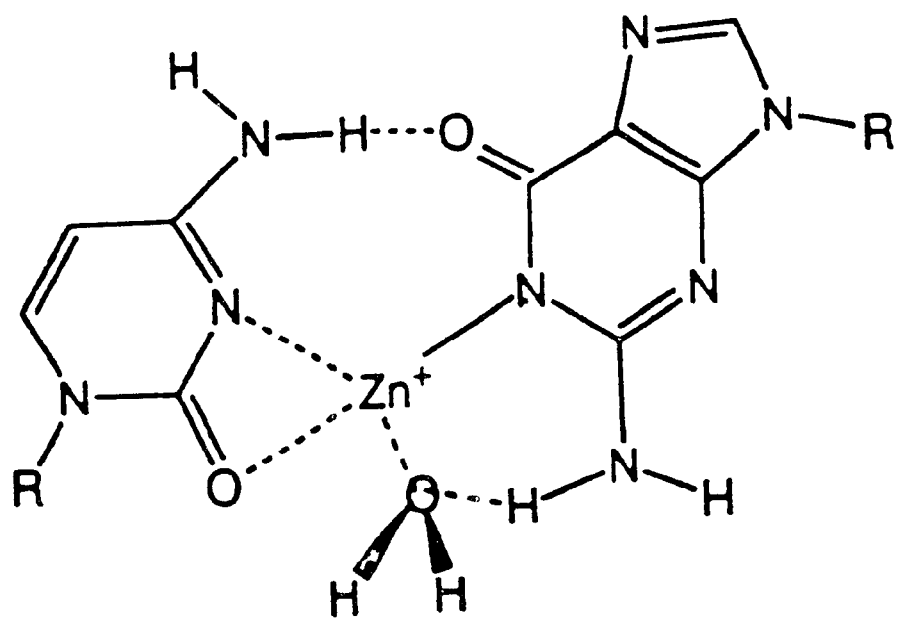
FIG. 2: shows a putative structure of M-DNA showing G-C and A-T base pairs. Putative hydrogen bonds and interactions between $Zn^{2+}$ and its coordinating groups are shown as dotted lines.
Figure 2:
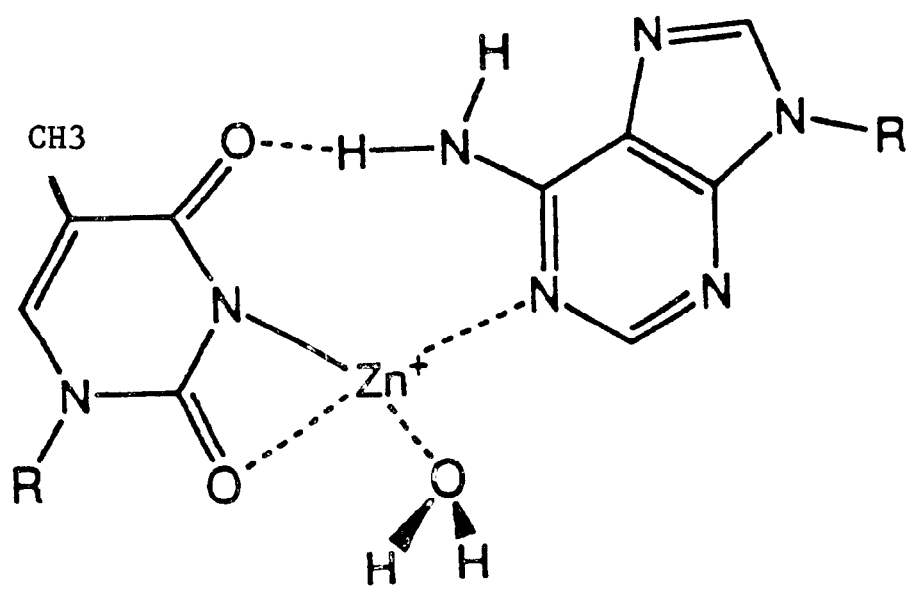

Based on these observations, a putative structure for M-DNA can be modelled as shown in FIG. 2. This model reflects experimental results relating to one aspect of the present invention, and does not limit the invention to any such putative structure. The model may nevertheless be helpful to others in practising routine variations of the invention. In this putative structure, the A-T and G-C base pairs are isomorphous, which is a common feature of stable helical nucleic acid structures (Paleck, 1991). Compared to a Watson-Crick base pair, insertion of the metal ion with an imino N-metal bond of 2 Å (Swaminathan and Sundralingham, 1979; DeMeester, 1973; McGall and Taylor, 1973) requires a 20°–30° rotation of the bases which opens up the minor groove. One hydrogen bond is retained in both base pairs, which may facilitate rapid reformation of normal B-DNA without denaturation of the helix on removal of the metal ion. The coordination geometry of the metal ion may be distorted square planar with the solvent providing the fourth ligand in some embodiments. The UV-Vis spectrum of the $Co^{2+}$ and $Ni^{2+}$ isomers of M-DNA have peaks in the visible with $\epsilon$ of 20 and 60 mol-1 cm-1 respectively; an observation which is consistent with this geometry (Lever, 1988). In this putative model of an M-DNA duplex, the metal ion is buried within the helix and d-$\pi$ bonding may occur with the aromatic bases above and below the metal ion. The putative model helix could be considered as a distorted member of the B-type helix family in agreement with the unremarkable CD spectrum (Lee et al, 1993.). On average the model metal-metal distance is 4 Å.

EXAMPLE 3
M-DNA is Nuclease Resistant

Figure 4:
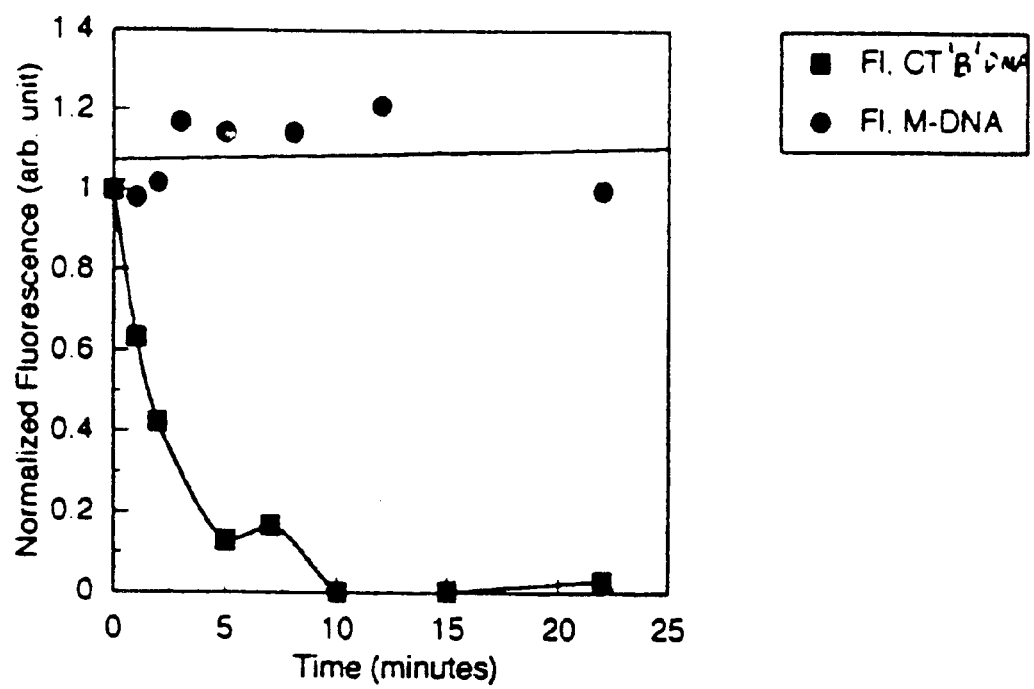
FIG. 4: shows the nuclease resistance of M-DNA. The amount of duplex DNA remaining as a function of time was assessed by the ethidium fluorescence assay (under conditions where M-DNA rapidly reverts to B-DNA, pH 8, 0.1 mM EDTA, so that ethidium can bind the DNA). The digestion was performed at 37° C. in 10 mM Tris-HCl, pH 7.4, 5 mM $MgCl_2$, 1 mM $NiCl_2$, 1 mg/ml gelatin, and 0.2 g/ml DNase I. The $Ni^{2+}$ form of M-DNA was preformed for the assay at pH 9 before adding it to the digestion buffer; B-DNA was added directly to the digestion buffer. The graph shows that the M-DNA is resistant to nuclease digestion while B-DNA is digested in about 10 minutes. The results also demonstrate that the $Ni^{2+}$ form of M-DNA is stable at physiological pH, a characteristic which facilitates the use of $Ni^{2+}$-M-DNA to mediate physiological responses in vivo, such as DNA immunization (in which the DNA 'vaccine' expresses an antigenic protein) or antisense applications (in which injected M-DNA inhibits the expression of a complementary gene).

The nuclease resistance of M-DNA was established by assaying the amount of duplex M-DNA remaining as a function of time in the presence of DNase I, as shown in FIG. 4. The amount of DNA was assessed by the ethidium fluorescence assay (under conditions where M-DNA rapidly reverts to B-DNA, i.e. pH 8 in the presence of EDTA, so that ethidium can bind the DNA for the purpose of the assay). The digestion was performed at 37° C. in 10 mM Tris-HCl, pH 7.4, 5 mM $MgCl_2$, 1 mM $NiCl_2$, 1 mg/ml gelatin, and 0.2 g/ml DNase I. The $Ni^{2+}$ form of M-DNA was preformed for the assay at pH 9, before adding it to the digestion buffer; B-DNA was added directly to the digestion buffer. The graph shows that the M-DNA is resistant to nuclease digestion while B-DNA is digested in about 10 minutes. The results also demonstrate that the $Ni^{2+}$ form of M-DNA is stable at physiological pH, a characteristic which may facilitate the use of Ni-M-DNA to mediate physiological responses in vivo, such as DNA immunization (in which the DNA vaccine expresses an antigenic protein) or antisense applications (in which injected M-DNA inhibits the expression of a gene).

EXAMPLE 4
M-DNA is Immunogenic

B-DNA is generally not immunogenic. However, synthetic or modified nucleic acids that are nuclease resistant may be capable of producing an antibody response under certain conditions (Braun and Lee, 1988).

To test the immunogenicity of M-DNA, Balb/C mice were immunized interperitoneally three times at ten day intervals with 10 µg of nickel-containing M-DNA, with and without methylated bovine serum albumin (Me-BSA). The first injection was with complete Freunds adjuvant and subsequent injections were with incomplete Freunds adjuvant. Three days after the final injection, blood was obtained by tail bleeding and the serum was tested for the present of antiM-DNA antibodies using nickel M-DNA coated polyvinylchloride plates in a SPIRA assay, using methods known in the art (Braun and Lee, 1988).

Figure 5:
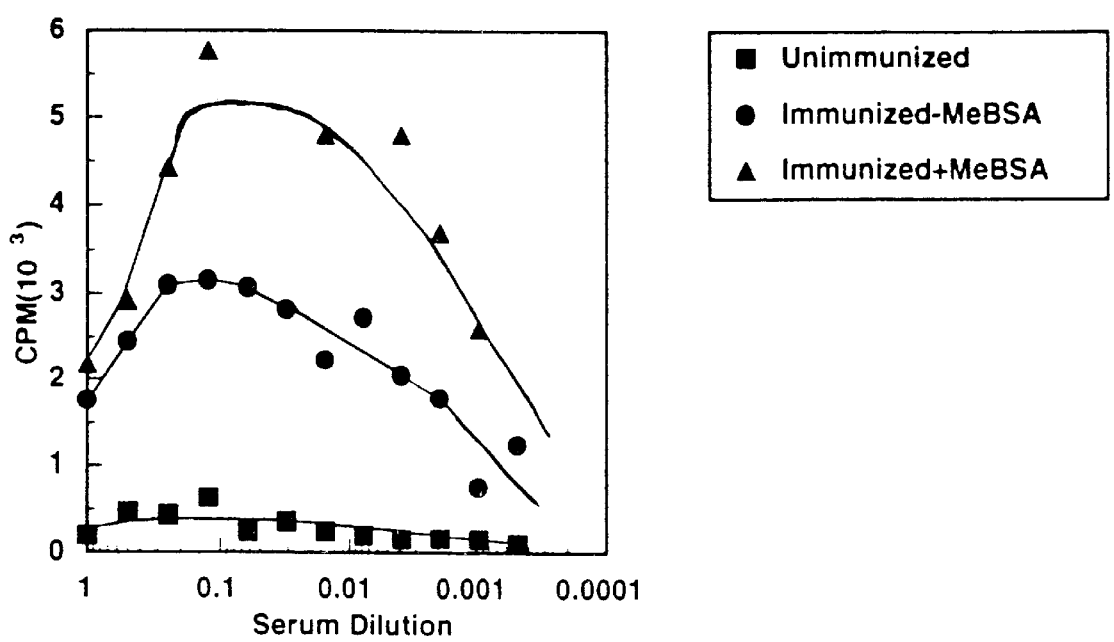
FIG. 5: shows that M-DNA is immunogenic. Balb/C mice were immunized interperitoneally three times at ten day intervals with 10 μg of nickel-containing M-DNA, with and without methylated bovine serum albumin (Me-BSA). The first injection was with complete Freunds adjuvant and subsequent injections were with incomplete Freunds adjuvant. Three days after the final injection, blood was obtained by tail bleeding and the serum was tested for the present of antiM-DNA antibodies using nickel M-DNA coated polyvinylchloride plates in a SPIRA assay, using methods known in the art (Braun and Lee, 1988).

The results, shown in FIG. 5, demonstrate that the mice immunized with M-DNA (with and without Me-BSA) show antibody titres to M-DNA up to about 1:1000 dilution. The control sera from an unimmunized mouse contains no antibodies to M-DNA. The ability of M-DNA to elicit an immune response is consistent with the finding that M-DNA may be nuclease resistant (see Braun and Lee, 1988). Accordingly, in some embodiments, M-DNA may be useful for immunizing a host, for example in methods as disclosed in U.S. Pat. Nos. 5,679,647; 5,804,566 or 5,830,877 issued to Carson et al. on; respectively Oct. 21, 1997, Sep. 8, 1998 and Nov. 3, 1998 (and incorporated herein by reference).

REFERENCES

1. Dandliker, P. J., Holmlin, R. E. & Barton, J. K. Science 275,1465–1468 (1997).
2. Hall, D. B., Holmlin, R. E. & Barton, J. K. Nature 382, 731–735 (1996).
3. Arkin, M. R., Stemp, E. D. A., Holmlin, R. E., Barton, J. K., Hormann, A., Olson, E. J. C. & Barbara, P. F. Science 273,475–479 (1996).
4. Murphy, C. J., Arkin, M. R., Jenkins, Y., Ghatlia, N. D., Bossmann, S. H., Turro, N. J. & Barton, J. K. Science 262,1025–1029 (1993).
5. Lewis, F. D., Wu, T., Zhang, Y., Letsinger, R. L., Greenfield, S. R., & Wasielewski, M. R. Science 277, 673–676 (1997).
6. Taubes, G. Science 275,1420–1421 (1997).
7. Lee, J. S., Latimer, L. J. P. & Reid, R. S. Biochem. Cell Biol. 71, 162–168 (1993).
8. Palecek, E. CRC Crit. Rev. Biochem. Mol. Biol. 26,151–226 (1991).
9. Yagil, G. CRC Crit. Rev. Biochem. Mol. Biol. 26, 475–559 (1991).
10. Swaminathan, V. & Sundralingham, M. CRC Crit. Rev. Biochem. Mol. Biol. 14, 245–336 (1979).
11. DeMeester, P., Goodgame, D. M. L., Skapski, A. C. & Warnke, Z. Biochem. Biophys. Acta 324,301–303 (1973).
12. McGall, M. J. & Taylor, M. R. Biochem. Biophys. Acta 390,137–139 (1973).
13. Lever, A. B. P. "Inorganic Electronic Spectroscopy" (Elsevier, Amsterdam) (1988).
14. Cheung, H. C. in "Topics in Fluorescence Spectroscopy" pp 128–171, ed. Lakowicz, J. R. (Plenum, New York) (1991).
15. Clegg, R. M. Methods in Enzymology 211,353–371 (1992).

16. Roesler, W. J., McFie, P. J. & Dauvin, C. J. Biol. Chem. 267, 21235–21243 (1992).
17. Lilley, D. M. J. & Clegg, R. M. Ann. Rev. Biophys. Biomol. Str. 22, 299–328 (1993).
18. Seeman, N. C. & Kallenbach, N. R. Ann. Rev. Biophys. Biomol. Str. 23, 53–86 (1994).
19. Brunger, A. 1. X-PLOR Manual, version 3.1 (rare University Press New Haven USA (1993).
20. Braun, R. P. and Lee, J. S. J. Immunol. v.141, 2084–2089 (1988).
21. Kessler, C. in *Nonisotopic Probing, Blotting and Sequencing,* L. J. Kricka, Ed., Academic Press (1995) pp. 3–40.
22. Haugland, R. P. *Handbook of Fluorescent Probes and Reserch Chemicals,* 6th Ed., p.157.

What is claimed is:

1. An electrical conductor comprising an electron source electrically coupled to a conductive metal-containing nucleic acid duplex, the conductive metal-containing nucleic acid duplex comprising a first strand of nucleic acid and a second strand of nucleic acid, the first and the second nucleic acid strands comprising a plurality of nitrogen-containing aromatic bases covalently linked by a backbone, the nitrogen-containing aromatic bases of the first nucleic acid strand being joined by hydrogen bonding to the nitrogen-containing aromatic bases of the second nucleic acid strand, the nitrogen-containing aromatic bases on the first and the second nucleic acid strands forming hydrogen-bonded base pairs in stacked arrangement along the length of the conductive metal-containing nucleic acid duplex, the hydrogen-bonded base pairs comprising an interchelated divalent metal cation coordinated to a nitrogen atom in one of the aromatic nitrogen-containing aromatic bases, to form the electrical conductor.

2. An electrical conductor comprising an electron source electrically coupled to a conductive metal-containing nucleic acid duplex, the conductive metal-containing nucleic acid duplex comprising a first strand of nucleic acid and a second strand of nucleic acid, the first and the second nucleic acid strands comprising a plurality of nitrogen-containing aromatic bases covalently linked by a backbone, the nitrogen-containing aromatic bases of the first nucleic acid strand being joined by hydrogen bonding to the nitrogen-containing aromatic bases of the second nucleic acid strand, the nitrogen-containing aromatic bases on the first and the second nucleic acid strands forming hydrogen-bonded base pairs in stacked arrangement along the length of the conductive metal-containing nucleic acid duplex, the hydrogen-bonded base pairs comprising an interchelated divalent metal cation coordinated to a nitrogen atom in one of the aromatic nitrogen-containing aromatic bases, wherein the divalent metal cation is selected from the group consisting of $Zn^{2+}$, $Co^{2+}$, and $Ni^{2+}$.

3. The electrical conductor of claim 2 further comprising an electron sink electrically coupled to the conductive metal-containing nucleic acid duplex.

4. The electrical conductor of claim 3 wherein the electron source is an electron donor molecule capable of donating an electron to the conductive metal-containing nucleic acid duplex.

5. The electrical conductor of claim 4 wherein the electron sink is an electron acceptor molecule capable of accepting an electron from the conductive metal-containing nucleic acid duplex.

6. The electrical conductor of claim 5 wherein the electron donor molecule is a fluorescent molecule.

7. The electrical conductor of claim 6 wherein the electron acceptor molecule is a fluorescent molecule.

8. The electrical conductor of claim 7 wherein the electron acceptor molecule is rhodamine.

9. The electrical conductor of claim 6 wherein the electron donor molecule is fluorescein.

10. The electrical conductor of claim 2 wherein the first and the second nucleic acid strands are deoxyribonucleic acid and the nitrogen-containing aromatic bases are selected from the group consisting of adenine, thymine, guanine and cytosine.

11. The electrical conductor of claim 2 wherein the divalent metal cations are substituted for imine protons of the nitrogen-containing aromatic bases, and the nitrogen-containing aromatic bases are selected from the group consisting of thymine and guanosine.

12. The electrical conductor of claim 2 wherein at least one of the aromatic nitrogen-containing aromatic bases is thymine, having an N3 nitrogen atom, and the divalent metal cation is coordinated by the N3 nitrogen atom.

13. The electrical conductor of claim 2 wherein at least one of the aromatic nitrogen-containing aromatic bases is guanine, having an N1 nitrogen atom, and the divalent metal cation is coordinated by the N1 nitrogen atom.

14. A method for making conductive metal-contaig nucleic acid duplexes comprising:
  a) providing a nucleic acid duplex comprising a first strand of nucleic acid and a second strand of nucleic acid, the first and the second nucleic acid strands comprising a plurality of nitrogen-containing aromatic bases covalently linked by a backbone, the nitrogen-ontaining aromatic bases of the first nucleic acid strand being joined by hydrogen bonding to the nitrogen-containing aromatic bases of the second nucleic acid strand, the nitrogen-containing aromatic bases on the first and the second nucleic acid strands forming hydrogen-bonded base pairs in stacked arrangement along the length of the nucleic acid duplex;
  b) subjecting the nucleic acid duplex to a basic solution in the presence of a divalent metal cation under conditions effective to form a conductive metal-containing nucleic acid duplex, wherein the hydrogen-bonded base pairs of the conductive metal-containing nucleic acid duplex comprise an interchelated divalent metal cation coordinated to a nitrogen atom in one of the aromatic nitrogen-containing aromatic bases;
  c) providing an electron source electrically coupled to the conductive metal-containing nucleic acid duplex, to form a conductive metal-containing nucleic acid duplex.

15. A conductive metal-containing nucleic acid duplex produced as a final product by the process of claim 14, comprising the electron source.

16. A method for making conductive metal-containing nucleic acid duplexes comprising:
  a) providing a nucleic acid duplex comprising a first strand of nucleic acid and a second strand of nucleic acid, the first and the second nucleic acid strands comprising a plurality of nitrogen-containing aromatic bases covalently linked by a backbone, the nitrogen-containing aromatic bases of the first nucleic acid strand being joined by hydrogen bonding to the nitrogen-containing aromatic bases of the second nucleic acid strand, the nitrogen-containing aromatic bases on the first and the second nucleic acid strands forming hydrogen-bonded base pairs in stacked arrangement along the length of the nucleic acid duplex;
  b) subjecting the nucleic acid duplex to a basic solution in the presence of a divalent metal cation under conditions effective to form a conductive metal-containing nucleic acid duplex, wherein the hydrogen-bonded base pairs of the conductive metal-containing nucleic acid duplex comprise an interchelated divalent metal cation coordinated to a nitrogen atom in one of the aromatic nitrogen-containing aromatic bases;
  c) providing an electron source electrically coupled to the conductive metal-containing nucleic acid duplex;
wherein the divalent metal cation is selected from the group consisting of $Zn^{2+}$, $Co^{2+}$, and $Ni^{2+}$.

17. The method of claim 16 further comprising providing an electron sink electrically coupled to the conductive metal-containing nucleic acid duplex.

18. The method of claim 17 wherein the nucleic acid duplex is a deoxyribonucleic acid duplex comprising nitrogen-containing aromatic bases selected from the group consisting of adenine, thymine, guanine and cytosine.

19. The method of claim 17 wherein the electron sink is an electron acceptor molecule capable of accepting an electron from the conductive metal-containing nucleic acid duplex.

20. The method of claim 19 wherein the electron acceptor molecule is a fluorescent molecule.

21. The method of claim 20 wherein the electron acceptor molecule is rhodamine.

22. The method of claim 16 wherein the conditions effective to form a conductive metal-containing nucleic acid duplex are effective to substitute the divalent metal cations for an imine proton of a nitrogen containing aromatic base in the nucleic acid duplex.

23. The method of claim 16 wherein the basic solution is pH 8.5 or greater.

24. The method of claim 16 wherein the electron source is an electron donor molecule capable of donating an electron to the conductive metal-containing nucleic acid duplex.

25. The method of claim 24 wherein the electron donor molecule is a fluorescent molecule.

26. The method of claim 25 wherein the electron donor molecule is fluorescein.

27. A conductive metal-containing nucleic acid duplex produced as a final product by the process of claim 16, comprising the electron source.

28. A method for detecting the formation of conductive metal-containing nucleic acid duplexes comprising:
   a) providing a first strand of nucleic acid;
   b) providing a second strand of nucleic acid;
   c) mixing the first strand of nucleic acid with the second strand of nucleic acid under conditions which allow complementary nucleic acid strands to hybridize;
   d) subjecting the mixed first and second nucleic acid strands to a basic solution in the presence of a divalent metal cation under conditions suitable for forming a conductive metal-containing nucleic acid duplex if the first and second nucleic acid strands are complementary, wherein the first and second nucleic acid strands comprising a plurality of nitrogen-containing aromatic bases covalently linked by a backbone, the nitrogen-containing aromatic bases of the first nucleic acid strand being joined by hydrogen bonding to the nitrogen-containing aromatic bases of the second nucleic acid strand, the nitrogen-containing aromatic bases of the first and the second nucleic acid strands forming hydrogen-bonded base pairs in stacked arrangement along the length of the conductive metal-containing nucleic acid duplex, the hydrogen-bonded base pairs comprising an interchelated divalent metal cation coordinated to a nitrogen atom in one of the aromatic nitrogen-containing aromatic bases to form an electrical conductor;
   e) providing an electron source electrically coupled to the conductive metal-containing nucleic acid duplex;
   f) assaying for conductance of electrons from the electron source, wherein the divalent metal cation is selected from the group consisting of $Zn^{2+}$, $Co^{2+}$, and $Ni^{2+}$.

29. The method of claim 28 further comprising providing an electron sink electrically coupled to the conductive metal-containing nucleic acid duplex.

30. The method of claim 29 wherein the electron sink is an electron acceptor molecule capable of accepting an electron from the conductive metal-containing nucleic acid duplex.

31. The method of claim 30 wherein the electron acceptor molecule is a fluorescent molecule.

32. The method of claim 31 wherein the electron acceptor molecule is rhodamine.

33. The method of claim 28 wherein the first and the second nucleic acid strands are deoxyribonucleic acid comprising nitrogen-containing aromatic bases selected from the group consisting of adenine, thymine, guanine and cytosine.

34. The method of claim 28 wherein the basic solution is pH 8.5 or greater.

35. The method of claim 28 wherein the electron source is an electron donor molecule capable of donating an electron to the conductive metal-containing nucleic acid duplex.

36. The method of claim 35 wherein the electron donor molecule is a fluorescent molecule.

37. The method of claim 36 wherein the electron donor molecule is fluorescein.

38. A method for detecting the formation of conductive metal-containing nucleic acid duplexes comprising:
   a. providing a first strand of nucleic acid;
   b. providing a second strand of nucleic acid;
   c. mixing the first strand of nucleic acid with the second strand of nucleic acid under conditions which allow complementary nucleic acid strands to hybridize;
   d. subjecting the mixed first and second nucleic acid strands to a basic solution in the presence of a divalent metal cation under conditions suitable for forming a conductive metal-containing nucleic acid duplex if the first and second nucleic acid strands are complementary, wherein the first and second nucleic acid strands comprising a plurality of nitrogen-containing aromatic bases covalently linked by a backbone, the nitrogen-containing aromatic bases of the first nucleic acid strand being joined by hydrogen bonding to the nitrogen-containing aromatic bases of the second nucleic acid strand, the nitrogen-containing aromatic bases of the first and the second nucleic acid strands forming hydrogen-bonded base pairs in stacked arrangement along the length of the conductive metal-containing nucleic acid duplex, the hydrogen-bonded base pairs comprising an interchelated divalent metal cation coordinated to a nitrogen atom in one of the aromatic nitrogen-containing aromatic bases to form an electrical conductor;
   e. providing an electron source electrically coupled to the conductive metal-containing nucleic acid duplex;
   f. assaying for conductance of electrons from the electron source.

39. The method of claim 38 wherein the conditions suitable for forming a conductive metal-containing nucleic acid duplex are effective to substitute the divalent metal cations for an imine proton of a nitrogen containing aromatic base in the nucleic acid duplex.

40. The method of claim 29 wherein the electron source is electrically coupled to the conductive metal-containing nucleic acid duplex by covalent attachment to the first strand of nucleic acid and the electron sink is electrically coupled to the conductive metal-containing nucleic acid duplex by covalent attachment to the second strand of nucleic acid.

41. The electrical conductor of claim 1 further comprising an electron sink electrically coupled to the conductive metal-containing nucleic acid duplex.

42. The electrical conductor of claim 41 wherein the electron source is an electron donor molecule capable of donating an electron to the conductive metal-containing nucleic acid duplex.

43. The electrical conductor of claim 41 wherein the electron sink is an electron acceptor molecule capable of accepting an electron from the conductive metal-containing nucleic acid duplex.

44. The electrical conductor of claim 42 wherein the electron sink is an electron acceptor molecule capable of accepting an electron from the conductive metal-containing nucleic acid duplex.

45. The electrical conductor of claim 44 wherein the electron donor molecule is a fluorescent molecule.

46. The electrical conductor of claim 42 wherein the electron donor molecule is a fluorescent molecule.

47. The electrical conductor of claim 43 wherein the electron acceptor molecule is a fluorescent molecule.

48. The electrical conductor of claim 44 wherein the electron acceptor molecule is a fluorescent molecule.

49. The electrical conductor of claim 45 wherein the electron acceptor molecuel is a fluorescent molecule.

50. The electrical conductor of claim 46 wherein the electron donor molecule is fluorescein.

51. The electrical conductor of claim 43 wherein the electron acceptor molecule is rhodamine.

52. The electrical conductor of claim 1 wherein the first and the second nucleic acid strands are deoxyribonucleic acid and the nitrogen-containing aromatic bases are selected from the group consisting of adenine, thymine, guanine and cytosine.

53. The electrical conductor of claim 41 wherein the first and the second nucleic acid strands are deoxyribonucleic acid and the nitrogen-containing aromatic bases are selected from the group consisting of adenine, thymine, guanine and cytosine.

54. The electrical conductor of claim 42 wherein the first and the second nucleic acid strands are deoxyribonucleic acid and the nitrogen-containing aromatic bases are selected from the group consisting of adenine, thymine, guanine and cytosine.

55. The electrical conductor of claim 43 wherein the first and the second nucleic acid strands are deoxyribonucleic acid and the nitrogen-containing aromatic bases are selected from the group consisting of adenine, thymine, guanine and cytosine.

56. The electrical conductor of claim 44 wherein the first and the second nucleic acid strands are deoxyribonucleic acid and the nitrogen-containing aromatic bases are selected from the group consisting of adenine, thymine, guanine and cytosine.

57. The electrical conductor of claim 45 wherein the first and the second nucleic acid strands are deoxyribonucleic acid and the nitrogen-containing aromatic bases are selected from the group consisting of adenine, thymine, guanine and cytosine.

58. The electrical conductor of claim 47 wherein the first and the second nucleic acid strands are deoxyribonucleic acid and the nitrogen-containing aromatic bases are selected from the group consisting of adenine, thymine, guanine and cytosine.

59. The electrical conductor of claim 1 wherein the divalent metal cation is selected from the group consisting of $Zn^{2+}$, $Co^{2+}$, and $Ni^{2+}$.

60. The electrical conductor of claim 41 wherein the divalent metal cation is selected from the group consisting of $Zn^{2+}$, $Co^{2+}$, and $Ni^{2+}$.

61. The electrical conductor of claim 42 wherein the divalent metal cation is selected from the group consisting of $Zn^{2+}$, $Co^{2+}$, and $Ni^{2+}$.

62. The electrical conductor of claim 43 wherein the divalent metal cation is selected from the group consisting of $Zn^{2+}$, $Co^{2+}$, and $Ni^{2+}$.

63. The electrical conductor of claim 44 wherein the divalent metal cation is selected from the group consisting of $Zn^{2+}$, $Co^{2+}$, and $Ni^{2+}$.

64. The electrical conductor of claim 45 wherein the divalent metal cation is selected from the group consisting of $Zn^{2+}$, $Co^{2+}$, and $Ni^{2+}$.

65. The electrical conductor of claim 47 wherein the divalent metal cation is selected from the group consisting of $Zn^{2+}$, $Co^{2+}$, and $Ni^{2+}$.

66. The electrical conductor of claim 52 wherein the divalent metal cation is selected from the group consisting of $Zn^{2+}$, $Co^{2+}$, and $Ni^{2+}$.

67. The electrical conductor of claim 53 wherein the divalent metal cation is selected from the group consisting of $Zn^{2+}$, $Co^{2+}$, and $Ni^{2+}$.

68. The electrical conductor of claim 54 wherein the divalent metal cation is selected from the group consisting of $Zn^{2+}$, $Co^{2+}$, and $Ni^{2+}$.

69. The electrical conductor of claim 55 wherein the divalent metal cation is selected from the group consisting of $Zn^{2+}$, $Co^{2+}$, and $Ni^{2+}$.

70. The electrical conductor of claim 56 wherein the divalent metal cation is selected from the group consisting of $Zn^{2+}$, $Co^{2+}$, and $Ni^{2+}$.

71. The electrical conductor of claim 1 wherein the divalent metal cations are substituted for imine protons of the nitrogen-containing aromatic bases, and the nitrogen-containing aromatic bases are selected from the group containing of thymine and guanosine.

72. The electrical conductor of claim 59 wherein the divalent metal cations are substituted for imine protons of the nitrogen-containing aromatic bases, and the nitrogen-containing aromatic bases are selected from the group consisting of thymine and guanosine.

73. The electrical conductor of claim 1 wherein at least one of the aromatic nitrogen- containing aromatic bases is thymine, having an N3 nitrogen atom, and the divalent metal cation is coordinated by the N3 nitrogen atom.

74. The electrical conductor of claim 59 wherein at least one of the aromatic nitrogen- containing aromatic bases is thymine, having an N3 nitrogen atom, and the divalent metal cation is coordinated by the N3 nitrogen atom.

75. The electrical conductor of claim 1 wherein at least one of the aromatic nitrogen- containing aromatic bases is guanine, having an N1 nitrogen atom, and the divalent metal cation is coordinated by the N1 nitrogen atom.

76. The electrical conductor of claim 59 wherein at least one of the aromatic nitrogen- containing aromatic bases is guanine, having an N1 nitrogen atom, and the divalent metal cation is coordinated by the N1 nitrogen atom.

\* \* \* \* \*